United States Patent [19]

Markham

[11] Patent Number: 4,774,948

[45] Date of Patent: Oct. 4, 1988

[54] MARKING AND RETRACTION NEEDLE HAVING RETRIEVABLE STYLET

[76] Inventor: Charles W. Markham, 667 Snug Island, Clearwater Beach, Fla. 33515

[21] Appl. No.: 934,332

[22] Filed: Nov. 24, 1986

[51] Int. Cl.$^4$ .............................................. A61B 17/34
[52] U.S. Cl. ............................. 128/329 R; 128/303 R
[58] Field of Search ................... 128/303 R, 751–754, 128/305, 329 R, 654; 604/164

[56] References Cited

U.S. PATENT DOCUMENTS 2,541,246  2/1951  Held ..................................... 128/305
4,592,356  6/1986  Gutierrez ..................... 128/334 R X Primary Examiner—Michael H. Thaler
Attorney, Agent, or Firm—A. W. Fisher, III

[57] ABSTRACT

A marking and retraction needle. An axially extending, slot-like opening is formed in the needle near its distal end, but is axially spaced therefrom. A stylet, in the form of an elongate thin wire, is slidingly received within the hollow needle and a portion near its distal end is bent back to form a barb-like member. The barb-like member extends through the opening formed in the needle when properly aligned, but the tip or distal end of the stylet remains within the needle at all times. The barb engages tissue and anchors the needle against movement during breast manipulation for X-rays or surgical scrubbing so that a tumor the location of which is marked by the needle can be surgically removed. The stylet is removed by advancing it axially, which advancement causes the barb to enter the extreme distal end of the needle and thus to withdraw from its engagement with tissue so that both the needle and the stylet may then be partially withdrawn, redirected and repositioned as needed. The stylet may also be totally withdrawn for specimen xerography or X-raying. The needle may also be used as a retractor during surgery. Three embodiments are shown.

6 Claims, 3 Drawing Sheets

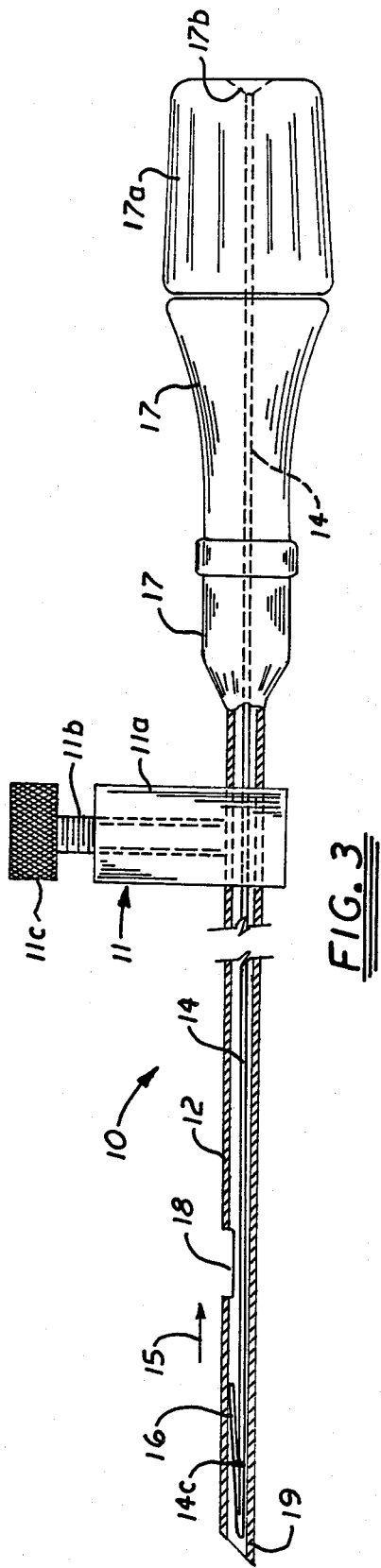
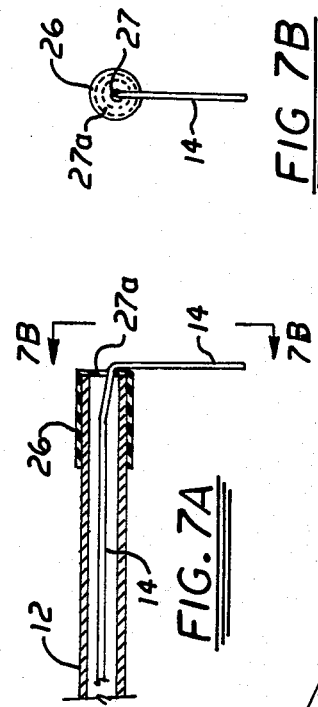
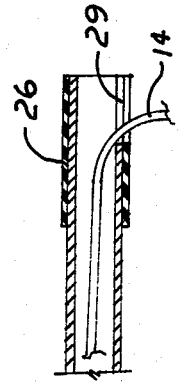
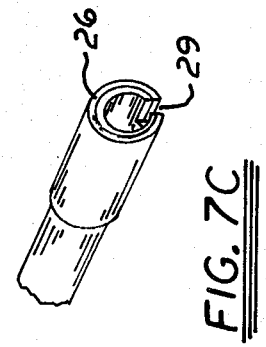
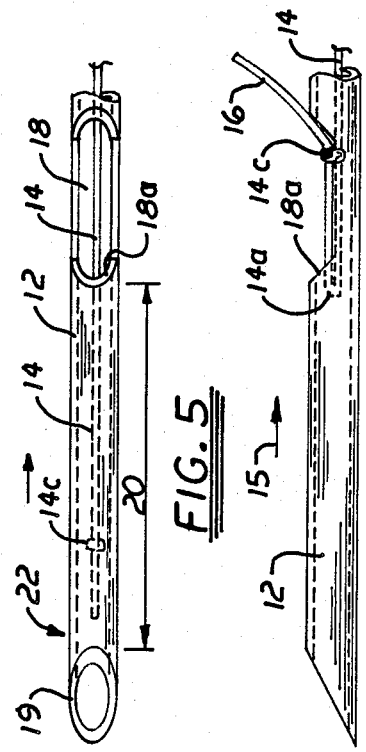
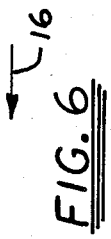

MARKING AND RETRACTION NEEDLE HAVING RETRIEVABLE STYLET

BACKGROUND OF THE INVENTION

1. Field of the Invention

This invention generally relates to marking and retraction needles of the type used to mark the location of tumors prior to surgery or to secure a prostate during surgery, respectively, and specifically relates to a marking and retraction needle having a retrievable stylet.

2. Description of the Prior Art

Small tumors in the breast are often removed by surgical procedures; obviously, the surgeon must be able to easily locate the tumor or area to be removed if unnecessary tissue removal is to be avoided.

The art has developed a device known as a marking needle or localizer that marks the location of the tumor to be removed. Preparatory to surgery, the tip of the needle is placed adjacent the tumor to be removed, and an anchoring means is employed to prevent the needle tip from extracting itself from its position adjacent the tumor.

The anchoring means now in widespread use is a stylet in the form of an elongate thin wire with a barb formed in its distal end, which stylet is received within a hollow needle.

When the needle is satisfactorily positioned, the stylet is axially advanced, i.e., it is pushed forwardly out of the needle. It is then retracted a very short distance so that the barb can engage and hook tissue. The needle is then removed, leaving the stylet behind. Since the proximal end of the stylet extends out of the patient's body, it remains visible and serves as the marker that guides the surgeon to the tumor.

There are a number of problems with the marking needle just described, even though it is in widespread use as aforesaid.

Once the stylet is in place, X-rays are taken to determine whether or not the stylet is in its optimal position. Typically, the breast will be compressed in two directions, i.e., it will be subjected to oppositely directed vertical forces and oppositely directed lateral forces. In other words, it is squeezed either up and down or left to right, or both, and X-rays are taken.

Unfortunately, the squeezing tends to drive the stylet in deeper because the compression urges the barb to burrow, i.e., to work itself in a forward direction.

If the stylet were not provided with a hook, however, the squeezing would cause the needle to work its way out of the patient's body.

Once the X-rays have been taken, it may be determined that the hooked stylet is not ideally positioned and that, accordingly, its position should be changed. However, relocation necessarily requires retraction of the stylet from the patient's body. The barb or hook prevents such retraction. In fact, the only way to remove the stylet is by surgery; this is ironic since the primary purpose of the stylet is to avoid unnecessary tissue removal.

The stylet left in the body to mark a tumor location may itself be cut inadvertently during the surgical attempt to remove the tumor. The stylet is a small gauge wire having a diameter of about a ten-thousandths of an inch (0.0010"). It is not easily seen and therefore is likely to be severed. In fact, it is severed frequently by the surgeon's scalpel. Obviously, since the stylet must be surgically removed as aforesaid, a severed stylet increases the difficulties faced by the surgeon.

The severing of the stylet may be avoided by slipping a protective tube over it, but this is not an entirely satisfactory solution to the problem since it necessitates use of the protective tube.

The benefit of being able to pinpoint a tumor prior to surgery outweighs the detriments associated with use of the conventional marking needle, however, and the art has simply accepted its shortcomings.

Marking needles are also used to to help anchor prostate glands against movement as required in certain surgical procedures. Many of the above-mentioned shortcomings also apply when the needles are used in prostate surgery. When used to anchor a gland against movement, the needles are known as retraction needles.

SUMMARY OF THE INVENTION

The present disclosure announces an important breakthrough in the art of marking and retracting needles.

The improved marking/retraction needle of the present invention includes a hollow needle which receives therein a stylet with a barb formed near its end, and the barb is employed to engage tissue to anchor the position of the stylet.

However, the barb may be disengaged from the tissue within which it is embedded, and the entire stylet may be non-surgically withdrawn from the body after its use as a tumor marker or as a retraction needle has been fulfilled.

Moreover, the novel stylet is protected against severing as well.

Thus, all of the shortcomings of the marking/retraction needle now in widespread use are eliminated by the invention disclosed herein. Thus, the present invention is pioneering in nature representing as it does an important breakthrough which solves a number of longstanding but heretofore unfulfilled needs.

The highly desirable properties of the present invention derive primarily from an opening of slot-like proportions which is provided near the distal end of the hollow needle.

The provision of the slot enables the barb to extend out of the opening and into tissue as desired without ever leaving the protective housing of the needle.

Thus, the needle and stylet are both left in place during the surgical removal of the tumor, the needle housing itself serving to protect the wire against inadvertent severing.

Then, when the surgery has been completed and the specimen has been X-rayed, the stylet may be advanced forwardly; since it has been embedded in tissue, some tissue will be wedgingly engaged in the crotch of the hook. As the stylet is advanced forwardly, the resilient barb is constrained to disengage from the tissue within which it had been embedded and to re-enter the needle through the slot. The needle is then easily removed and the tissue is step-sectioned.

The opening is spaced near the distal end of the needle as aforesaid, but sufficiently far therefrom so that advancement of the stylet by an amount sufficient to cause the re-entry of the barb into the needle housing does not result in the distal end of the stylet exiting the opening at the extreme distal tip of the needle.

With the stylet advanced as aforesaid, both needle and stylet can be retracted from the body or redirected and repositioned.

In a first embodiment of the invention, the proximal end of the stylet is anchored in a cap member which assures that the distal end of the stylet cannot exit the needle.

In a second embodiment, the cap member is eliminated and the stylet can be advanced in a proximal to distal direction and made to exit the distal end of the needle if desired.

In the second embodiment, a crimped-on tube protects the stylet.

In a third embodiment, the cap member is again eliminated and the stylet is not protected by a crimped-on tube but the needle has a closed, cone-shaped end that prevents the stylet from exiting the distal end of the needle.

It is the primary object of this invention to provide a marking/retraction needle having a barbed stylet housed therewithin that may be retrieved in the absence of surgical procedures.

Other objects of this invention include the provision of different embodiments of the marking/retraction needle to enhance its versatility.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 3 is a side elevational, partly in section view of a first embodiment of the invention, which view includes a first embodiment of a needle holding means of the type shown in FIG. 2A;

FIG. 5 is a top plan view of a portion of the novel device, showing the barbed stylet in its housed position;

FIG. 6 is a side elevational view of that portion of the invention shown in FIG. 5, but showing the barb on the stylet extending outwardly of the opening formed in the needle;

FIG. 7A is a view similar to that of FIG. 7 but showing a third embodiment where the stylet is not protected by a tube and where the proximal end of the stylet is bent at a ninety degree angle so that it cannot travel in a proximal to distal direction;

FIG. 7B is an end view taken along line 7B—7B in FIG. 7A;

FIG. 7C is a perspective view of the end of shrink tubing member 26, showing a wedge-shaped slot formed therein that is used with the third embodiment of the invention, i.e., where the stylet is not sheathed within a tube;

FIG. 7D is a side elevational view of the embodiment shown in FIG. 7C, showing the stylet 14 bent through the slot shown in FIG. 7C.

Similar reference numerals refer to similar parts throughout the several views of the drawings.

DETAILED DESCRIPTION OF THE PREFERRED EMBODIMENTS

Figure 1A:
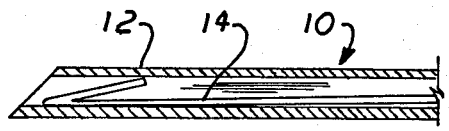
FIG. 1A shows a marking needle of the prior art with a retracted stylet barb.
Figure 1B:
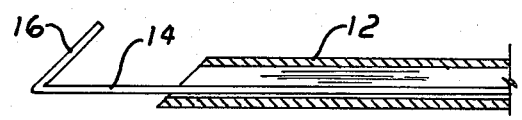
FIG. 1B shows the prior art marking needle of FIG. 1A with its barbed stylet in its extended, tissue-engaging position.

Reference will first be made to FIGS. 1A and 1B which FIGS. depict a marking/retraction needle of the prior art.

Needle 10 includes hollow needle member 12 and stylet 14 housed therewithin.

The operation of the tool shown in said FIGS. is as follows: needle member 12 is inserted to mark the location of a tumor, and upon withdrawal of the needle 12 stylet member 14 is held against withdrawal and thus emerges from the distal end of needle member 12 which position is depicted in FIG. 1B. Stylet 14 is then retracted slightly so that the barb portion thereof can engage tissue and thus anchor the stylet against further movement. Removal of stylet 14 and its barb 16 is accomplished surgically.

Figure 2A:
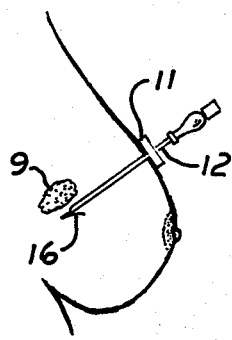
FIG. 2A is a diagrammatic representation of a breast having a tumor therein the location of which is indicated by a first embodiment of the marking and retraction needle of the present invention.
Figure 2B:
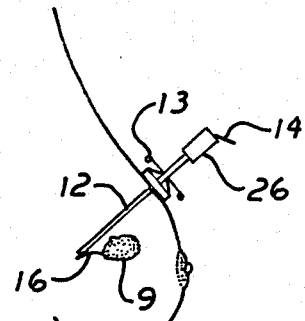
FIG. 2B is a view similar to that of FIG. 2A, but showing a second embodiment of a means for holding the needle in place.

Reference should now be made to FIGS. 2A and 2B which diagrammatically depict a first and second embodiment of the novel device in their respective operative positions. The positioning depicted is alternative and any of the embodiments shown herein can be positioned in either of the two positions shown.

In the position shown in FIG. 2A, the needle is being used as a marking needle since its position is denoting the location of a tumor 9; in the position of FIG. 2B, the device is being used as a retraction needle since the tumor is positioned in the crotch of the barb.

In both FIGS., needle holding members 11, 13 are shown positioned against the surface of the patient's skin, depressing the skin as shown. Needle holders 11, 13 serve as needle locking means in that they are effective to secure the position of needle member 12 against unwanted proximal to distal axial movement, i.e., the function of holders 11, 13 is to prevent needle 12 from going deeper into the patient's tissue.

Figure 3A:
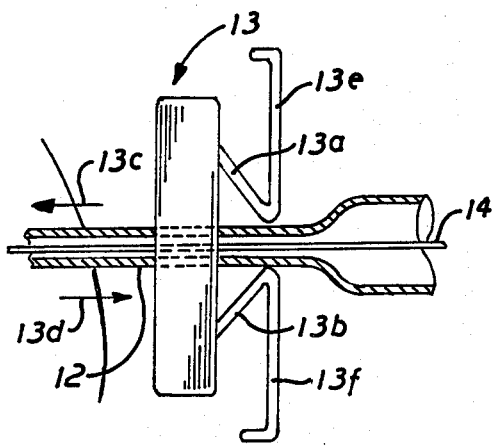
FIG. 3A is a side elevational, partly in section view of a second embodiment of a needle holding means of the type shown in FIG. 2B.

Holder 11 is shown in better detail in FIG. 3 whereas holder 13 is better shown in FIG. 3A.

FIG. 3 shows that in the first embodiment of the invention, stylet 14 is protected along its length either by needle 12 or by a hub member 17 and cap member 17a. Moreover, it will be noted in FIG. 3 that stylet 14 is anchored at its proximal end, being securely engaged to mounting member 17b.

It is clear from an inspection of FIG. 3 that cap member 17a prevents stylet 14 from exiting the distal end of the needle 12.

Figure 3B:
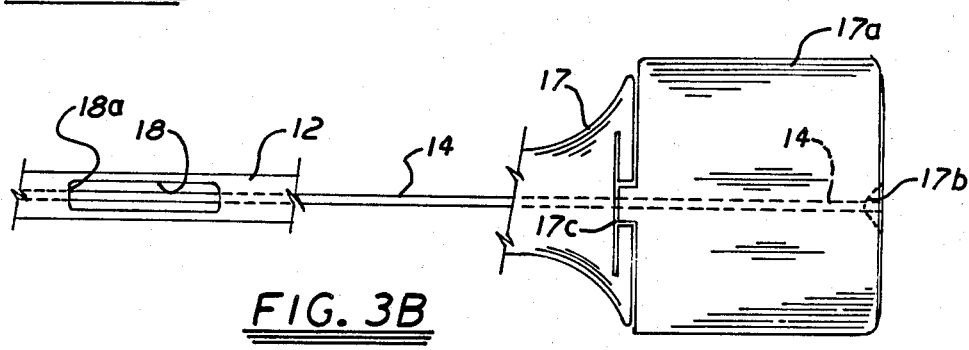
FIG. 3B is a fragmentary plan view of the embodiment shown in FIG. 3.

The interconnection between hub 17 and cap 17a is by a key means formed in cap 17a and a key way formed in hub 17, said key and key way means being denoted generally by the reference numeral 17c in FIG. 3B.

Although holder 11 could take many forms, in FIG. 3 it has the form of a disc or wafer member 11a having a set screw 11b and a handle 11c which when rotated advances or retracts screw 11b as desired. When advanced, set screw 11b locks wafer 11a into position relative to needle 12 so that needle 12 cannot advance any further into the patient's tissue, as perhaps best understood in connection with FIG. 2A.

FIG. 3A depicts the needle holder 13 in more detail as aforesaid. An annular member 13 has resilient, diametrically opposed arms 13a, 13b which prevent sliding movement of needle member 12 in the direction indicated by arrow 13c but which allows movement of needle 12 in the direction indicated by arrow 13d. Gripper members 13e, 13f are integral with arms 13a, 13b; the physician disengages the arms 13a, 13b from the needle by pressing the ends of gripper members 13a, 13b in the respective directions indicated by the unnumbered directional arrows adjacent said ends.

As shown in FIG. 2B, needle holding member 13 is pressed against the surface of the patient's skin as aforesaid when in use; member 13 is shown spaced away from the patient's body in FIG. 3A to simplify the drawing.

FIG. 3 also shows that needle 12 has a port or opening 18 formed therein near its distal end 19.

Figure 4:
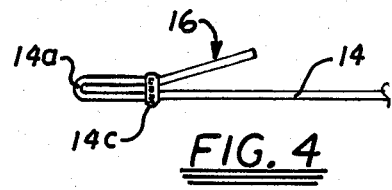
FIG. 4 is an enlarged view of the distal end of the novel stylet showing a first form of stylet retraction limiting means.
Figure 4A:
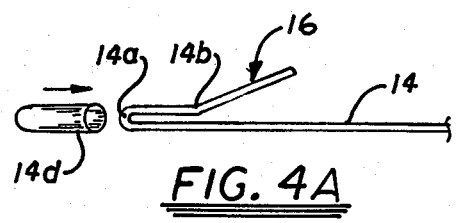
FIG. 4A is an enlarged view similar to that of FIG. 4 but showing a second form of a stylet retraction limiting means.

FIGS. 4 and 4A show the construction of the novel barb 16 in detail. Reference numerals 14c and 14d refer to a weld and a cap member which serve to retain the shape of the barb.

Barb 16 is positioned near the distal end of stylet 14 and is formed by two bends in said stylet.

The first bend is a 180 degree return bend 14a and the second bend 14b forms an acute angle between the bent portion of the stylet and its unbent portion as depicted.

Thus, the second bend 14b is resilient. As is clear from an inspection of FIG. 3, retraction of stylet 14 in the direction indicated by directional arrow 15 (being the distal to proximal direction) will allow barb 16 to project outwardly of needle 12 when barb 16 aligns with the aforementioned opening 18 formed in needle 12.

Referring now to FIG. 5, said opening 18 is there shown in plan view. The axial dimension of the opening 18 must be at least large enough to allow barb 16 to protrude therefrom in the manner depicted in FIG. 6.

It is conceivable that stylet 14 could be retracted too far by the physician, resulting in the distal tip 14a of the stylet exiting opening 18 if no stylet retraction limiting means were provided.

Accordingly, weld 14c is positioned a sufficient distance from tip 14a to prevent this unwanted occurrence. FIG. 6 shows that the distance between the tip 14a of the stylet and weld 14c is sufficient to prevent retraction of tip 14a through opening 18. Weld 14c is thus understood to be a stylet retraction limiting means.

In any configuration where the distance between tip 14a and weld 14c is greater than the length of opening 18, the distal tip 14a of the stylet will not be able to escape the stylet through said opening 18.

It is important to observe the difference between FIGS. 1B (a prior art depiction) and FIG. 6; in both FIGS., barb 16 is operatively deployed and in engagement with tissue.

However, in FIG. 6, barb 16 is still under the direct control of the physician whereas the barb in FIG. 1B is no longer under such direct control, i.e., it cannot be retracted into needle 12 by any means and its removal from the patient must be accomplished surgically.

As indicated in FIG. 5, the distance indicated by the reference numeral 20 separates the distal end 18a of opening 18 and the distal tip 19 of needle member 12.

When stylet 14 is axially advanced in the direction of directional arrow 21 in FIG. 6, barb 16, being flexible, retracts into opening 18 and becomes housed in that portion of needle member 12 denoted 22 in FIG. 5, said portion having the length dimension indicated by dimension-indicating arrow 20.

Thus, barb 16 is fully housed within needle member 12 in FIG. 5 and both needle 12 and stylet 14 with barb 16 can be retracted.

Accordingly, surgical removal of stylet 14 and barb 16 is not needed and the primary object of the invention is ingenuously achieved.

Figure 7:
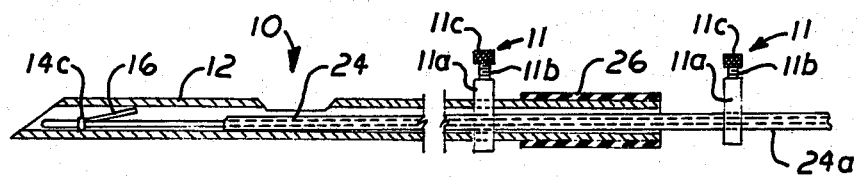
FIG. 7 is a longitudinal sectional view of a second embodiment of the present invention where the stylet is protected along its extent by a crimped-on tube.

A second embodiment of the present invention is shown in FIG. 7.

The embodiment of FIG. 7 eliminates hub 17 and cap member 17a, thereby significantly reducing the cost of manufacturing device 10.

The elimination of said hub and cap members also eliminates the protective shield for stylet 14, so it becomes necessary to provide a protective means for stylet 14 in lieu of hub 17 and cap 17a.

The protective means is denoted 24 in FIG. 7. It is a crimped-on tube within which stylet 14 is received. Tube 24 is rigid and serves as a protective sheath for stylet 14.

Shrink tubing member 26, shown in FIG. 7 at the proximal end of needle 12, provides a holding means for the physician using device 10.

Member 26 is not absolutely needed in either the second or the third embodiments of this invention.

There are many ways to maintain stylet 14 against unwanted proximal-to-distal travel after it has been placed in its desired position as depicted in FIGS. 2A and 2B.

For example, as in the second embodiment, tube 24 extends proximally beyond shrink tube member 26 in the manner depicted in FIG. 7 and a holder 11 as shown or another holder such as holder 13 could be employed to retain it and hence stylet against proximal to distal travel. The rigid tube 24 allows the use of a holder 11, it being understood that no such holder could be applied directly to stylet 14 without breaking the same.

Those skilled in the are will appreciate that the holder 11 on the left hand side of FIG. 7 would abut the patient's skin as depicted in FIG. 2A whereas the holder 11 on the right hand side of FIG. 7 would be positioned in abutting relation to the proximal end of member 26, i.e., to the left of the position illustrated, in order to prevent unwanted proximal to distal travel of stylet 14 and to assist in moving the stylet in to retract the barb.

A third embodiment is depicted in FIG. 7A; tube 24 is shown terminating distally of the proximal end of member 26, but it should be understood that in the third embodiment the tube is not used at all since no holder 11 or 13 is employed in the manner depicted on the right hand side of FIG. 7.

Instead, the stylet 14 alone extends proximally from the end of the tube 24. A wedge-shaped slot 27 formed in a plug 27a that plugs shrink tube member 26 as shown in FIG. 7B is provided so that stylet 14 may be bent in the manner depicted in FIGS. 7A and 7B whereby the wedging relation of stylet 14 and slot 27 prevents unwanted burrowing of said stylet.

Another alternative is shown in FIGS. 7C and 7D which show a slot 29 formed in shrink tubing member 26 along its extent so that stylet 14 may be wedged thereinto when bent as shown in FIG. 7D.

Again, although tube 24 is shown in FIG. 7D, it is superfluous; in both FIGS. 7A as aforesaid and in FIG. 7D, the drawings should be construed as not showing tube 24.

However, it should be noted that in the embodiment of FIG. 7, the right hand holder member 11 could be obviated, member 26 could be slotted as shown in FIG. 7C, and the tube 24 could be bent so that it is wedgingly retained by slot 29 in the same manner as depicted in FIG. 7D for the stylet 14.

Figure 8:
FIG. 8 is a view showing the pencil pointed needle used in connection with the third embodiment of the invention.

FIG. 8 shows a needle 12 terminating in a pencil point 30; since pencil point 30 is closed, the stylet 14 can not exit needle 12 by undergoing proximal to distal travel in this embodiment.

The stylet holding means shown in FIGS. 7A-7D are intended for use in connection with the pencil point needle of FIG. 8.

This invention is a pioneering invention because it provides the first retractable barbed stylet. Accordingly, its other features are pioneering as well. For example, the hub and cap embodiment represesnts a significant breakthrough in the art, but the hubless and capless embodiments represent significant advances beyond even said hub and cap embodiment.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A needle having utility as a marking needle or as a retraction needle comprising:
    a hollow needle member having a proximal end adapted to be held by an individual and having a distal end adapted to penetrate tissue;
    a stylet member having a proximal and a distal end slidable received within said hollow needle member;
    a single resilient barb including a return bend formed on said distal end of said stylet member and an acute angle bend formed on said stylet member at the proximal end of said return bend;
    a slot including a proximal and distal end formed in said distal end of said hollow needle member;
    and a stylet retraction limiting means formed on said single resilient barb in spaced relationship relative to the distal end of said single resilient barb, the axial length of said spaced relationship being greater than the axial length of said slot;
    said stylet retraction limiting means including a weld positioned proximal relative to said return bend formed on said stylet member and said acute angle bend begins proximal to said weld
    such that when said single resilient barb is positioned distally relative to said slot, said hollow needle member houses said single resilient barb and when said stylet member is retracted in a distal to proximal direction a portion of said single resilient barb extends outwardly from said slot and said stylet retraction limiting means engages the proximal end of said slot to retain said distal end of said single resilient barb within said hollow needle member whereby as said stylet member is advanced in a proximal to distal direction said single resilient barb reenters said hollow needle member.

2. The needle of claim 1 further comprising a needle holding means to prevent proximal to distal movement of said hollow needle member relative to the surface of a patient's skin when said hollow needle member is operably positioned.

3. The needle of claim 2 wherein said needle holding means includes a centrally apertured disc member to receive said hollow needle member, said centrally apertured disc member including a set screw member operable to set the position of said apertured disc member relative to said hollow needle member when said screw member is axially advanced to engage said hollow needle member, said centrally apertured disc member abutting the surface of the patient's skin when said centrally apertured disc member is operably positioned.

4. A needle having utility as a marking needle or as a retraction needle comprising:
    a hollow needle member having a proximal end adapted to be held by an individual and having a distal end adapted to penetrate tissue;
    a stylet member having a proximal and a distal end slidably received within said hollow needle member;
    a single resilient barb including a return bend formed on said distal end of said stylet member and an acute angle bend formed on said stylet member at the proximal end of said return bend;
    a slot including a proximal and distal end formed in said distal end of said hollow needle member;
    and a stylet retraction limiting means formed on said single resilient barb in space relationship relative to the distal end of said single resilient barb, the axial length of said spaced relationship being greater than the axial length of said slot;
    said stylet retraction limiting means including a cap member positioned distally relative to said acute angle bend formed on said stylet member in surrounding, capping relationship relative to said return bend of said stylet member;
    such that when said single resilient barb is positioned distally relative to said slot, said hollow needle member houses said single resilient barb and when said stylet member is retracted in a distal to proximal direction a portion of said single resilient barb extends outwardly from said slot and said stylet retraction limiting means engages the proximal end of said slot to retain said distal end of said single resilient barb within said hollow needle member whereby as said stylet member is advanced in a proximal to distal direction said single resilient barb reenters said hollow needle member.

5. The needle of claim 4 further comprising a needle holding means to prevent proximal to distal movement of said hollow needle member relative to the surface of a patient's skin when said hollow needle member is operably positioned.

6. The needle of claim 5 wherein said needle holding means includes a centrally apertured disc member to receive said hollow needle member, said centrally apertured disc member including a set screw member operable to set the position of said apertured disc member relative to said hollow needle member when said screw members is axially advanced to engage said hollow needle member, said centrally apertured disc member abutting the surface of the patient's skin when said centrally apertured disc member is operably positioned.

* * * * *